United States Patent [19]

Sorg

[11] Patent Number: 4,892,879

[45] Date of Patent: Jan. 9, 1990

[54] 1-SUBSTITUTED-4-(THIAZOLYL-2-)-PIPERAZINES, -PIPERIDINES AND TETRAHYDRO-PYRIDINES USEFUL AS ANXIOLTIC, PSYCHOGERIATRIC, ANTISEPRESSANT AND ANTISCHIZIPHRENIC AGENTS

[75] Inventor: Dieter Sorg, Bern, Switzerland

[73] Assignee: Sandoz Pharm. Corp., E. Hanover, N.J.

[21] Appl. No.: 151,349

[22] Filed: Feb. 2, 1988

Related U.S. Application Data

[62] Division of Ser. No. 876,617, Jun. 20, 1986, Pat. No. 4,737,500.

[30] Foreign Application Priority Data

| Jun. 22, 1985 | [DE] | Fed. Rep. of Germany | ....... | 3522354 |
| Jun. 22, 1985 | [DE] | Fed. Rep. of Germany | ....... | 3522353 |
| Jun. 22, 1985 | [DE] | Fed. Rep. of Germany | ....... | 3522351 |
| Feb. 24, 1986 | [DE] | Fed. Rep. of Germany | ....... | 3605868 |

[51] Int. Cl.$^4$ .................. A61K 31/435; C07D 417/14
[52] U.S. Cl. .................................... 514/338; 546/198; 546/270; 514/321
[58] Field of Search ................ 546/198, 270; 548/126, 548/152, 165, 207, 134, 146, 215, 217, 305, 304, 358, 100, 468; 514/338, 359, 362, 365, 367, 369, 372, 373, 374, 375, 376, 386, 387, 414, 415, 422, 321

[56] References Cited

U.S. PATENT DOCUMENTS

| 3,331,843 | 7/1967 | Tomcufcik et al. | ................. | 544/360 |
| 3,489,757 | 1/1970 | Koppe et al. | ........................ | 544/369 |
| 3,717,634 | 2/1973 | Wu et al. | ............................. | 544/360 |
| 3,822,267 | 7/1974 | Sorg | ..................................... | 544/368 |
| 4,064,244 | 12/1977 | Sorg | ..................................... | 544/369 |
| 4,182,763 | 1/1980 | Casten et al. | ........................ | 544/357 |
| 4,737,500 | 4/1988 | Sorg | ..................................... | 514/252 |

FOREIGN PATENT DOCUMENTS 7204539  10/1972  Netherlands .

OTHER PUBLICATIONS

Derwent Abstract 86441R (1970).
Derwent Abstract 84-078401/13 (1984).
Derwent Abstract 66538D (1981).
Derwent Abstract 83-828300/48 (1983).
Derwent Abstract 83-797402/43 (1983).
J. of Med. Chem., vol. 12, pp. 860-865 (1969).
J. of Med. Chem., vol. 12, pp. 865-870 (1969).
Derwent Abstract 83-706657/28 (1983).
Derwent Abstract 85-000957/01 (1984).
Derwent Abstract 85-298807/48 (1985).
The Merck Index, Item 9398 (1983).
Chemical Abstracts 75:31808x (1971).
Chemical Abstracts 67:90839r (1967).
Chemical Abstracts 82:112035q (1975).
Derwent Abstract 76419U (1973).
Derwent Abstract 26334 E/13 (1982).
Chemical Abstracts 97:216011e (1982).

Primary Examiner—Cecilia Shen
Attorney, Agent, or Firm—Gerald D. Sharkin; Robert S. Honor; Joseph J. Borovian

[57] ABSTRACT

Thiazoles or pharmaceutically acceptable acid addition salts thereof are useful as anxiolytic, psychogeriatric, antidepressant and antischizophrenic agents.

5 Claims, No Drawings

1-SUBSTITUTED-4-(THIAZOLYL-2-)-PIPERAZINES, -PIPERIDINES AND TETRAHYDRO-PYRIDINES USEFUL AS ANXIOLTIC, PSYCHOGERIATRIC, ANTISEPRESSANT AND ANTISCHIZIPHRENIC AGENTS

This is a division of application Ser. No. 876,617, filed June 20, 1986, now issued as U.S. Pat. No. 4,737,500.

The present invention relates to novel thiazoles, processes for their production, pharmaceutical compositions containing them and their use as pharmaceuticals.

More particularly, the present invention relates to compounds of formula I,

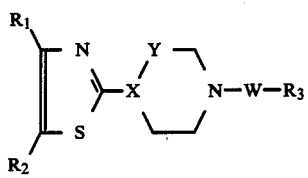

wherein $R_1$ and $R_2$ independently are hydrogen, $(C_{1-6})$alkyl, $(C_{3-6})$cycloalkyl, $(C_{3-6})$cycloalkyl$(C_{1-3})$alkyl, phenyl, phenyl$(C_{1-3})$alkyl or $R_1$ and $R_2$ signify together trimethylene, tetramethylene or pentamethylene, optionally substituted at the same or different carbon atoms by 1 or 2 methyl groups, or $R_1$ and $R_2$ signify together $-(CH_3)_2C-O-C(CH_3)_2-$, $R_1$ may additionally signify trifluoromethyl, W is alkylene of 2 to 6 carbon atoms, or alkenylene or alkynylene of 4 to 6 carbon atoms, whereby the unsaturation is not adjacent to the nitrogen atoms, X—Y is N—CH$_2$, C=CH or CH—CH$_2$ and $R_3$ is a group of formula (a)–(n)

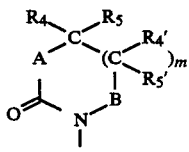 (a)

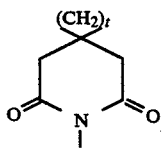 (b)

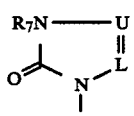 (c)

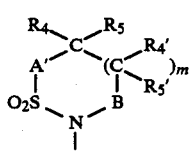 (d)

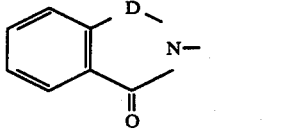 (e)

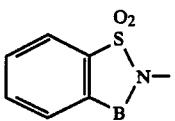 (f)

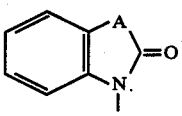 (g)

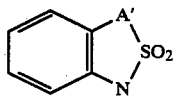 (h)

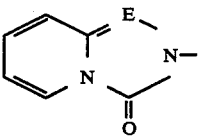 (i)

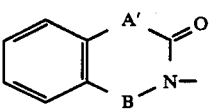 (j)

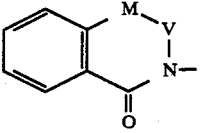 (k)

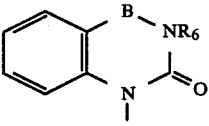 (l)

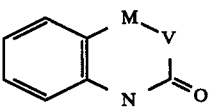 (m)

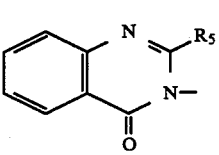 (n)

in which
A is

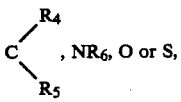

B is

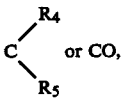

m is 0 or 1,

R$_4$ and R$_4'$ independently are hydrogen or (C$_{1-4}$)alkyl,

R$_5$ and R$_5'$ independently are hydrogen, (C$_{1-4}$)alkyl, phenyl or phenyl(C$_{1-4}$)alkyl, t is 4 or 5, R$_6$ is hydrogen or (C$_{1-3}$)alkyl, R$_7$ is hydrogen, (C$_{1-3}$)alkyl, phenyl(C$_{1-3}$)alkyl or phenoxy(C$_{1-3}$)alkyl, U=L is N=CR$_5$ or CR$_5$=N, A' is

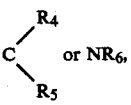

D is

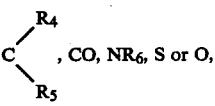

E is N or CH,

M—V is or

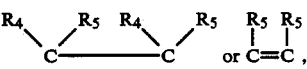

and when X—Y is N—CH$_2$, R$_3$ may also be a group of formula (o)

(o)

wherein

R$_8$ is hydrogen or (C$_{1-3}$)alkyl,

R$_9$ is —COR$_{10}$, —CON(R$_{11}$)R$_{12}$, —SO$_2$R$_{10}$ or —SO$_2$N(R$_{11}$)R$_{12}$, wherein R$_{10}$ is (C$_{1-6}$)alkyl, (C$_{3-6}$)cycloalkyl, phenyl or phenyl(C$_{1-3}$)alkyl, wherein each phenyl is optionally mono- or independently di- or trisubstituted by (C$_{1-3}$)alkyl, hydroxy, methoxy, methylenedioxy, amino, halogen or trifluoromethyl, R$_{11}$ and R$_{12}$ are each, independently, hydrogen or (C$_{1-3}$)alkyl or R$_{11}$ and R$_{12}$ together signify tetramethylene or pentamethylene, provided that when W is dimethylene and R$_9$ is —COR$_{10}$, wherein R$_{10}$ is 4-aminophenyl, at least one of R$_1$, R$_2$ and R$_8$ is other than hydrogen, and acid addition salts thereof.

Compounds of formula I, wherein W is alkenylene, can occur as cis/trans isomers. These isomers are also included within the scope of the present invention.

In one group of compounds of formula I,

R$_1$ and R$_2$ are independently hydrogen, (C$_{1-6}$)alkyl, (C$_{3-6}$)cycloalkyl, (C$_{3-6}$)cycloalkyl(C$_{1-3}$)alkyl, phenyl, phenyl(C$_{1-3}$)alkyl or R$_1$ and R$_2$ signify together trimethylene, tetramethylene or pentamethylene, optionally substituted at the same or different carbon atoms by 1 or 2 methyl groups, R$_1$ may additionally signify trifluoromethyl, W is alkylene of 2 to 6 carbon atoms, X—Y is N—CH$_2$ and R$_3$ is a group of formula (a)–(n), in which A is

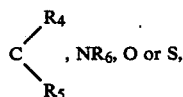

B is

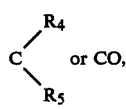

m is 0 or 1,

R$_4$ and R$_4'$ independently are hydrogen or (C$_{1-4}$)alkyl,

R$_5$ and R$_5'$ independently are hydrogen, (C$_{1-4}$)alkyl, phenyl or phenyl(C$_{1-4}$)alkyl, t is 4 or 5, R$_6$ is hydrogen or (C$_{1-3}$)alkyl, R$_7$ is hydrogen, (C$_{1-3}$)alkyl, phenyl(C$_{1-3}$)alkyl or phenoxy(C$_{1-3}$)alkyl, U=L is N=CR$_5$ or CR$_5$=N, A' is

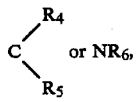

D is

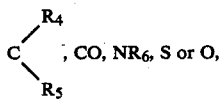

E is N or CH,

M—V is

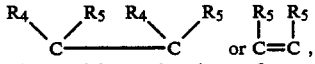

and acid addition salts thereof.

In another group of compounds of formula I, X—Y is N—CH$_2$ and R$_3$ is a group of formula (a), wherein A is CH$_2$, B is CO, m is 1, R$_4'$ and R$_5'$ are each hydrogen, R$_4$ and R$_5$ are each methyl, and either W is tetramethylene and R$_1$ and R$_2$ are the same and signify hydrogen or methyl, or R$_1$ is methyl, trifluoromethyl, tert. butyl or cyclopentyl and R$_2$ is hydrogen, or R$_1$ is hydrogen and R$_2$ is 2-methylpropyl or R$_1$ and R$_2$ signify together pentamethylene, or W is dimethylene, trimethylene, pentamethylene or hexamethylene, R₁ is tert. butyl and R₂ is hydrogen and acid addition salts thereof.

In another group of compounds of formula I, X—Y is N—CH₂ and R₃ is a group of formula (f), wherein B is CO, W is tetramethylene, and either R₁ is tert. butyl and R₂ is hydrogen or R₁ and R₂ together signify pentamethylene and acid addition salts thereof.

In another group of compounds, X—Y is N—CH₂ and R₃ is a group of formula (i), wherein E is N, W is trimethylene or tetramethylene, R₁ is tert. butyl and R₂ is hydrogen and acid addition salts thereof.

In one compound of formula I, X—Y is N—CH₂ and R₃ is a group of formula (b), wherein t is 4, R₁ and R₂ together signify pentamethylene and W is tetramethylene as well as acid addition salts thereof. In another compound of formula I, X—Y is N—CH₂ and R₃ is a group of formula (a), wherein A is CH₂, R₄ and R₅ are each hydrogen, m is 0, B is CH₂, W is tetramethylene, R₁ is tert. butyl and R₂ is hydrogen and acid addition salts thereof.

In another group of compounds of formula I, R₁ and R₂ are independently hydrogen, (C₁₋₆)alkyl, (C₃₋₆)cycloalkyl, (C₃₋₆)cycloalkyl(C₁₋₃)alkyl, phenyl, phenyl(C₁₋₃)alkyl, or R₁ and R₂ signify together trimethylene, tetramethylene or pentamethylene, W is alkylene of 2 to 6 carbon atoms, X—Y is C=CH or CH—CH₂, and R₃ is a group of formula (a)-(n), in which A is

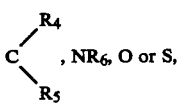, NR₆, O or S,

B is

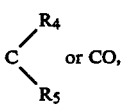 or CO, m is 0 or 1,

R₄ and R₄' independently are hydrogen or (C₁₋₄)alkyl,

R₅ and R₅' independently are hydrogen, (C₁₋₄)alkyl, phenyl or phenyl(C₁₋₄)alkyl, t is 4 or 5, R₆ is hydrogen or (C₁₋₃)alkyl, R₇ is hydrogen, (C₁₋₃)alkyl, phenyl(C₁₋₃)alkyl or phenoxy(C₁₋₃)alkyl, U=L is N=CR₅ or CR₅=N, A' is

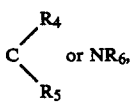 or NR₆,

D is

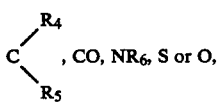, CO, NR₆, S or O,

E is N or CH, and

M—V is

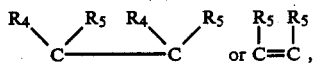

and acid addition salts thereof.

In still another group of compounds of formula I,

R₁ and R₂ independently are hydrogen, (C₁₋₆)alkyl, (C₃₋₆)cycloalkyl, (C₃₋₆)cycloalkyl(C₁₋₃)alkyl, phenyl, phenyl(C₁₋₃)alkyl, or R₁ and R₂ signify together trimethylene, tetramethylene or pentamethylene optionally substituted at the same or different carbon atoms by 1 or 2 methyl groups, R₁ may additionally signify trifluoromethyl, W is alkylene of 2 to 6 carbon atoms, X—Y is N—CH₂ and R₃ is a group of formula (o), wherein R₈ is hydrogen or (C₁₋₃)alkyl, R₉ is —COR₁₀, —CON(R₁₁)R₁₂, —SO₂R₁₀ or —SO₂N(R₁₁)R₁₂, wherein R₁₀ is (C₁₋₆)alkyl, (C₃₋₆)cycloalkyl, phenyl or phenyl(C₁₋₃)alkyl, wherein each phenyl is optionally mono- or independently di- or trisubstituted by (C₁₋₃)alkyl, hydroxy, methoxy, methylenedioxy, amino, halogen or trifluoromethyl, R₁₁ and R₁₂ are each, independently, hydrogen or (C₁₋₃)alkyl or R₁₁ and R₁₂ together signify tetramethylene or pentamethylene, provided that when W is dimethylene and R₉ is —COR₁₀, wherein R₁₀ is 4-aminophenyl, at least one of R₁, R₂ an R₈ is other than hydrogen, and acid addition salts thereof.

Any alkyl radical of 1 to 6 carbon atoms is preferably of 1 to 4 carbon atoms. Cycloalkyl or the cycloalkyl moiety of cycloalkylalkyl is conveniently cyclopentyl, cyclobutyl or cyclopropyl. Halogen is preferably chlorine or fluorine and especially chlorine.

For the above formula I, the following significances, as well as combinations thereof are preferred:

R₁ is preferably alkyl, especially tert. butyl or trifluoromethyl.

R₂ is preferably hydrogen.

W is preferably alkylene, especially dimethylene, trimethylene or tetramethylene.

X—Y is preferably N—CH₂ or C=CH.

R₃ is preferably a group of formula (a), (b), (f), (g), (i), (j) or (o).

In a preferred group of formula (a), A is CH₂, B is CO, m is 1, R₄' and R₅' are each hydrogen, and R₄ and R₅ are each methyl. In another preferred group of formula (a), A is CH₂, B is CH₂, m is 0, and R₄ and R₅ are each hydrogen.

In the preferred group of formula (b), t is 4.

In the preferred group of formula (f), B is CO. Preferably in group (g), A is NH.

In the preferred group of formula (i), E is N.

The preferred group (j) is the group wherein A' is CH₂ and B is CO.

In group (o), R₈ is preferably hydrogen R₉ is preferably —COR₁₀ or —SO₂R₁₀. R₁₀ is preferably phenyl, optionally mono- or independently di- or trisubstituted by methoxy or chlorine.

The present invention in another aspect provides a process for the production of a compound of formula I which comprises (a) producing a compound of formula Ia

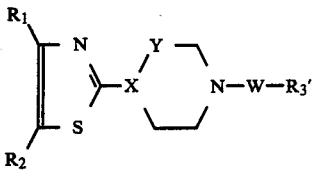

Ia wherein $R_1$, $R_2$, W and X—Y are as defined above, and $R_3'$ is a group of formula (a)–(n), or an acid addition salt thereof, by reacting a compound of formula II

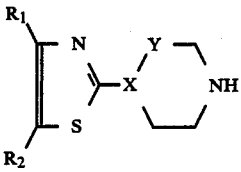

II wherein $R_1$, $R_2$ and X—Y are as defined above, with a compound of formula III

   III

Q—W—$R_3'$ wherein W and $R_3'$ are as defined above, and Q is a leaving group, or (b) producing a compound of formula Ib,

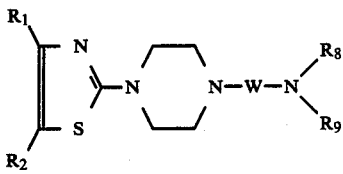

Ib wherein $R_1$, $R_2$, W, $R_8$ and $R_9$ are as defined above or an acid addition salt thereof, by reacting a compound of formula IV,

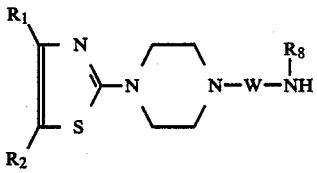

IV wherein $R_1$, $R_2$, W and $R_8$ are as defined above, with a compound of formula V,

   V

Z—$R_9$ wherein $R_9$ is as defined above and Z is a leaving group, and recovering the compound of formula I in free base form or acid addition salt form.

Process (a) may be effected in conventional manner. The reaction is conveniently carried out in an organic solvent. Suitable solvents include dimethylformamide, dioxane or acetonitrile. Conveniently, an acid binding agent, e.g. potassium carbonate, is present. In compounds of formula III the leaving group Q is for example halogen, e.g., chlorine or bromine, or —O—SO$_2$—$R_{13}$, wherein $R_{13}$ is ($C_{1-4}$)alkyl, phenyl or 4-tolyl.

Process (b) may be effected in conventional manner for analogous reactions. In compounds of formula V, Z is for example chlorine, bromine, —OCOOC$_2$H$_5$, —O—COOCH═CH$_2$ or —O—($C_{1-4}$)alkoxy. The process is conveniently carried out in an inert organic solvent such as tetrahydrofuran. Conveniently, an acid-binding agent, e.g., triethylamine, is present. The presence of an acid binding agent is not necessary when compounds of formula V, wherein Z is O-($C_{1-4}$)alkoxy, are utilized.

Compounds of formula II can be prepared by dealkylating or debenzylating a compound of formula VI,

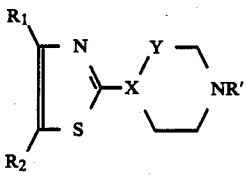

VI wherein $R_1$, $R_2$ and X—Y are as defined above, and R' is ($C_{1-6}$)alkyl or benzyl, or an acid addition salt thereof.

The dealkylation or debenzylation can be carried out in conventional manner, e.g., with haloformic acid esters, such as chloroformic acid ester, e.g. alkyl or vinyl ester, or with bromocyanide.

Compounds of formula IV, wherein $R_8$ is hydrogen, can be prepared by reducing a compound of formula IX,

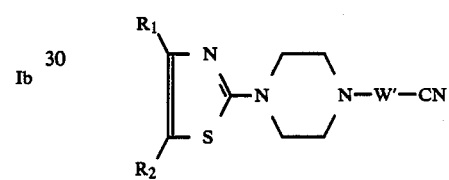

IX wherein $R_1$ and $R_2$ are as defined above and W' is alkylene of 1 to 5 carbon atoms, or alkenylene or alkenylene of 3 to 5 carbon atoms, whereby the unsaturation is not adjacent to the nitrogen atom. The reduction may be effected with lithium aluminum hydride, diborane or with sodium borohydride in the presence of a transition metal salt, e.g. cobaltous chloride. Alkylation of the resulting compound leads to compounds of formula IV wherein $R_8$ is alkyl.

Compounds of formula IX can be prepared by e.g. reacting a compound of formula II, wherein X—Y is N—CH$_2$ and $R_1$ and $R_2$ are as defined above, with an ω-halogeno-alkyl-, -alkenyl- or -alkynyl-nitrile.

Insofar as the production of starting materials is not particularly described, these compounds are known or may be produced in analogous manner to known compounds or to processes described herein.

A cis/trans mixture can be separated in known manner into the corresponding cis and trans components.

The compounds of formula I may be converted into acid addition salts thereof in conventional manner and vice versa. Suitable acids include for example, hydrochloric acid, hydrobromic acid, methanesulfonic acid, maleic acid or fumaric acid.

In the following examples all temperatures are given in degrees centigrade and are uncorrected.

In the Tables, the following abbreviations are used:
(1) hydrochloride
(2) maleinate
(3) methanesulfonate
(4) hydrogenmaleinate
(5) dihydrochloride

EXAMPLE 1

2-(4-(4-(4-(1,1-Dimethylethyl)-2-thiazolyl)-1-(1,2,3,6-tetrahydropyridinyl))butyl)-1,2-benzisothiazol-3-(2H)one-1,1-dioxide [compound of formula Ia]

3 g 2-(4-Bromobutyl)-1,2-benzisothiazol-3-(2H)one-1,1-dioxide, 2.1 g 4-(4-(1,1-dimethylethyl)-2-thiazolyl)-1,2,3,6-tetrahydropyridine, 1.4 $K_2CO_3$, 40 ml dimethylformamide and 5 ml water are stirred at room temperature for about 15 hours. The reaction mixture is diluted with water, extracted twice with ethyl ether, the combined ether extracts are washed with water, dried ($Na_2SO_4$) and evaporated. The oily residue is dissolved in ethanol and treated with maleic acid to give the hydrogenmaleinate of the title compound (1:1), m.p. 176°–177° (ethyl acetate/ethanol).

The starting material may be obtained as follows:

(a)
4-(4-(1,1-Dimethylethyl)-2-thiazolyl)-4-oxy-1-phenylmethyl-piperidine 6.7 g 1-Phenylmethyl-piperidin-4-one in 20 ml of abs. tetrahydrofuran are added dropwise under argon at −60° to −50° to a stirred suspension of 5 g 2-(4-(1,1-dimethylethyl)-thiazolyl)-lithium in 50 ml of abs. tetrahydrofuran. The mixture is stirred at slowly increasing temperature for 15 hours. Moisture containing tetrahydrofuran is added and the mixture evaporated. The residue is partitioned between water and ethyl ether, the ether phase dried ($Na_2SO_4$) and evaporated. The residue is chromatographed on silica gel (ethyl acetate) to give the heading compound as a light yellow oil. M.p. of the methanesulfonate is 184°–185°.

(b)
4-(4-(1,1-Dimethylethyl)-2-thiazolyl)-1-phenylmethyl-1,2,3,6-tetrahydropyridine 8 g (4-(4-(1,1-dimethyl-ethyl)-2-thiazolyl)-4-oxy-1-phenylmethylpiperidine and 100 g polyphosphoric acid are heated at 130° for 6 hours. The mixture is carefully treated with ice at 80°, diluted with ice-water, made alkaline with aqueous NaOH solution and extracted 3 times with ethyl ether. The combined extracts are washed with saturated brine solution, filtered and dried ($Na_2SO_4$). Upon addition of ethanolic maleic acid, the hydrogenmaleinate of the heading compound, m.p. 182°–183° (ethyl acetate/hexane) is obtained.

(c)
4-(4-(1,1-Dimethylethyl)-2-thiazolyl)-1,2,3,6-tetrahydropyridine 5.5 g 4-(4-(1,1-dimethylethyl)-2-thiazolyl)-1-phenylmethyl-1,2,3,6-tetrahydropyridine, 2.5 g $K_2CO_3$ and 50 ml 1,2-dichloroethane are treated dropwise at −10° to −7° under stirring with 3.75 ml chloroformic acid vinyl ester. The mixture is stirred at −10° to −7° for 3 hours. The solvent is evaporated, the residue partitioned between water and hexane. and the water phase extracted with hexane. The combined organic layers are washed with saturated brine solution, filtered and dried ($Na_2SO_4$). The solvent is evaporated and the oily residue is added under ice-cooling to 20% aqueous hydrochloric acid. The mixture is heated on a steam bath for 4 hours, then cooled to room temperature and extracted once with dichloromethane.The aqueous acidic solution is filtered, made alkaline with aqueous NaOH and extracted with ethyl ether. After evaporation of ether, the heading compound is obtained as an oily residue. M.p. of the hydrogenmaleinate is 170°–171°.

EXAMPLE 2

4,4-Dimethyl-1-(4-(4-((1,1-dimethylethyl)-2-tniazolyl)-1-piperidinyl)-butyl)-2,6-piperidin-dione [compound of formula Ia]

To a stirred mixture of 1.1 9.4-(4-(1,1-dimethylethyl)-2-thiazolyl)-piperdine, 0.7 g $K_2CO_3$, 15 ml dimethylformamide and 7 ml water are added 1.35 g 1-(4-bromobutyl)-4,4-dimethyl-2,6-piperidin-dione in 10 dimethylformamide. The mixture is stirred at 40° for 15 hours. The solvent is evaporated and the residue partitioned between ethyl ether and water. Tne ether phase is dried and evaporated. The oily-residue is treated with ethanolic maleic acid whereby the hydrogenmaleinate of the title compound, m.p. 184°–186° (ethanol/ether), is obtained.

The starting material may be obtained as follows:

(a)
4-(4-(1,1-Dimethylethyl)-2-thiazolyl)-1-phenylmethyl-piperidine 3 g of the Example 1(b) compound in 70 ml etnanol are hydrogenated in the presence of 1 g 5% palladium on charcoal at room temperature and normal pressure. The mixture is filtered and evaporated, whereby the title compound crystallizes out, m.p. 56°, m.p. of the hydrogenmaleinate is 170°.

(b) 4-(4-(1,1-Dimethylethyl)-2-thiazolyl)-piperidine 4.8 g 4-(4-(1,1-Dimethylethyl)-2-thiazolyl)-1-phenylmethyl-piperidine, 2 g $K_2CO_3$ and 50 ml 1,2-dicnloroethane are treated dropwise at −5° under stirring with 3.2 g chloroformic acid vinyl ester. The mixture is stirred 2 hours at room temperature and evaporated. The residue is partitioned between ethyl ether and water. The ether phase is evaporated and the residue dissolved in 30 ml metnanol and 30 ml 20% aqueous hydrochloric acid. The mixture is heated 1 hour at 60 and evaporated. The residue is partitioned between aqueous NaOH and ether. The etner phase is treated with maleic acid to yield the hydrogenmaleinate of the title compound, m.p. 141°–142° (ethanol/ether).

EXAMPLE 3

2-(4-(4-((1,1-dimethylethyl)-2-thiazolyl)-1-piperidinyl)-butyl)-1,2-benzisothiazol-3-(2H)-one-1,1-dioxide [compound of formula Ia]

In a manner analogous to that described in Example 2, the title compound is produced, m.p. of the hydrogenmaleinate is 187°–189°.

EXAMPLE 4

4,4-Dimethyl-1-(4-(4-(4-(1,1-dimethylethyl)-2-thiazolyl)-1-piperazinyl)butyl)-2,6-piperidin-dione [compound of formula Ia]

4 g 1-(4-Bromobutyl)-4,4-dimethyl-2,6-piperidin-dione, 3.15 g 1-(4-(1,1-dimethylethyl)-2-thiazolyl)-piperazine, 2.7 g $K_2CO_3$, 70 ml dimethylformamide and 20 ml water are stirred at room temperature for about 35 hours. The mixture is diluted with water, extracted twice with ether, the combined extracts are washed with water, dried ($Na_2SO_4$) and evaporated. The residue is recrystallized from hexane/ethyl acetate, whereby the title compound is obtained, m.p. 93°–94°. M.p. of the hydrochloride is 199°–201° (ethanol/ether).

EXAMPLE 5

4,4-Dimethyl-1-(4-(4-(4-trifluoromethyl-2-thiazolyl)-1-piperazinyl)butyl)-2,6-piperidin-dione [compound of formula Ia]

6.2 g 1-(4-Bromobutyl)-4,4-dimetnyl-2,6-piperidindione, 4.7 g 1-(4-trifluoromethyl-2-thiazolyl)-piperazine, 2.8 g K$_2$CO$_3$ and 200 ml acetonitrile are stirred at 60°–70° for 24 hours. The mixture is filtered, evaporated and the residue partitioned between ether and aqueous NaOH. The etner phase is washed with water, dried and evaporated. Upon addition of ethanolic maleic acid, the maleinate of the title compound is obtained, m.p. 159°–161°.

The starting material may be obtained as follows:

(a) 4-Methyl-1-(4-trifluoromethyl-2-thiazolyl)-piperazin

To a solution of 33.9 g 1-bromo-3,3,3-trifluoro-2-propanone in 300 ml of absolute ethanol are added 28.6 g 4-methyl-1-piperazinylthiocarboxamide. The mixture is refluxed for 4 hours, evaporated to dryness and the residue partitioned between ethyl ether and aqueous NaOH. The ether phase is washed, dried and evaporated, whereby the title compound is obtained, m.p. 62° (ethyl acetate/hexane).

(b) 1-(4-Trifluoromethyl-2-thiazolyl)-piperazine

In a manner analgous to that described in Example 1(c), the title compound is obtained, m.p. of the maleinate is 162°.

EXAMPLE 6

In a manner analgous to that described in Example 4, the following compounds of formula Ia are obtained, wherein X—Y is N—CH$_2$ and W is —(CH$_2$)$_n$—:

| Ex. | R$_1$ | R$_2$ | n | R$_3$ | m.p. |
|---|---|---|---|---|---|
| a | C(CH$_3$)$_3$ | H | 4 | 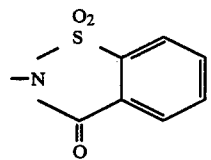 | 150–151°[2] |
| b | C(CH$_3$)$_3$ | H | 2 | 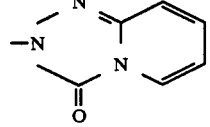 | 128–130° |
| c | C(CH$_3$)$_3$ | H | 2 | 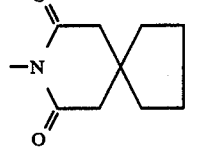 | 99° |
| d | C(CH$_3$)$_3$ | H | 4 | 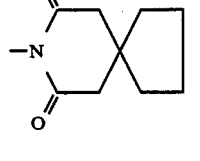 | 179–180°[3] |
| e | C(CH$_3$)$_3$ | H | 3 | 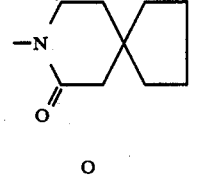 | 138–140°[2] |
| f | C(CH$_3$)$_3$ | H | 2 | 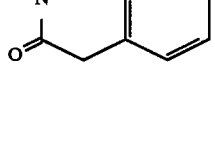 | 160°[2] |

-continued

| Ex. | R₁ | R₂ | n | R₃ | m.p. |
|---|---|---|---|---|---|
| g | C(CH₃)₃ | H | 2 | 1H-benzimidazol-2(3H)-one, N-substituted | 94–95° |
| h | C(CH₃)₃ | H | 3 | 1H-benzimidazol-2(3H)-one, N-substituted | 118–119° |
| i | C(CH₃)₃ | H | 4 | 1H-benzimidazol-2(3H)-one, N-substituted | 184–185°² |
| j | CH₃ | H | 4 | 4,4-dimethyl-2,6-dioxopiperidin-1-yl | 105–106° |
| k | C(CH₃)₃ | H | 6 | 4,4-dimethyl-2,6-dioxopiperidin-1-yl | 173–175°¹ |
| l | C(CH₃)₃ | H | 5 | 4,4-dimethyl-2,6-dioxopiperidin-1-yl | 198–199°¹ |
| m | C(CH₃)₃ | H | 3 | 4,4-dimethyl-2,6-dioxopiperidin-1-yl | 230–233°¹ |
| n | C(CH₃)₃ | H | 2 | 4,4-dimethyl-2,6-dioxopiperidin-1-yl | 185°² |
| o | —(CH₂)₅— | | 4 | 4,4-dimethyl-2,6-dioxopiperidin-1-yl | 121–122° |

-continued

| Ex. | R₁ | R₂ | n | R₃ | m.p. |
|---|---|---|---|---|---|
| p | H | H | 4 | 3,3-dimethylglutarimide-N-yl | 179–180°[2] |
| q | CH₃ | CH₃ | 4 | 3,3-dimethylglutarimide-N-yl | 143–144°[2] |
| r | cyclopentyl | H | 4 | 3,3-dimethylglutarimide-N-yl | 180°[2] |
| s | H | CH₂CH(CH₃)₂ | 4 | 3,3-dimethylglutarimide-N-yl | 167–168°[2] |
| t | —(CH₂)₅— | | 4 | benzisothiazolinone-S,S-dioxide-N-yl | 176–177°[2] |
| u | CH₃ | H | 4 | benzisothiazolinone-S,S-dioxide-N-yl | 160–161°[2] |
| v | —(CH₂)₅— | | 4 | 3-azaspiro[5.4]decane-2,4-dione-N-yl | 120–121° |
| w | C(CH₃)₃ | H | 3 | pyrido-triazinone | 166–167°[2] |
| x | C(CH₃)₃ | H | 4 | pyrido-triazinone | 93–95°[2] |

-continued

| Ex. | $R_1$ | $R_2$ | n | $R_3$ | m.p. |
|---|---|---|---|---|---|
| y | $C(CH_3)_3$ | H | 4 | pyrrolidin-2-one (N-linked) | 179–181°[1] |
| z | H | H | 4 | 2,3-dihydro-1,2-benzisothiazol-3-one 1,1-dioxide (N-linked) | 133–134° |
| ab | $CH_3$ | H | 2 | 4,4-dimethylpiperidine-2,6-dione (N-linked) | 121–122° |
| ac | $CF_3$ | H | 4 | 2,3-dihydro-1,2-benzisothiazol-3-one 1,1-dioxide (N-linked) | 197–198[2]<br>106–107 |
| ad | $-(CH_3)_2C-O-C(CH_3)_2-$ | | 4 | 4,4-dimethylpiperidine-2,6-dione (N-linked) | 87°[2] |
| ae | $CF_3$ | H | 4 | pyrrolidin-2-one (N-linked) | 98–100°[2] |

EXAMPLE 7

In a manner analogous to that described in Example 4, the following compounds of formula Ia are obtained, wherein X—Y is N—$CH_2$:

| Ex. | $R_1$ | $R_2$ | W | $R_3$ | m.p. |
|---|---|---|---|---|---|
| a | $C(CH_3)_3$ | H | $CH_2-CH=CHCH_2$ | 4,4-dimethylpiperidine-2,6-dione (N-linked) | 158–160°[2] |
| b | $C(CH_3)_3$ | H | $CH_2C{\equiv}CCH_2$ | 2,3-dihydro-1,2-benzisothiazol-3-one 1,1-dioxide (N-linked) | 225–230°[1] |

-continued

| Ex. | R₁ | R₂ | W | R₃ | m.p. |
|---|---|---|---|---|---|
| c | C(CH₃)₃ | H | CH₂C≡CCH₂ | 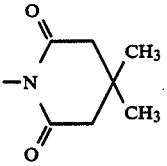 | 108° |
| d | C(CH₃)₃ | H | CH₂CH=CHCH₂ | 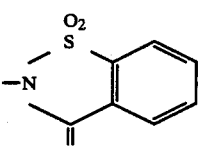 | 97–98°* |

*trans

EXAMPLE 8

5-Chloro-2-methoxy-N-(2-(4-(4-(1,1-dimethylethyl)-2-thiazolyl)-1-piperazinyl)ethyl)-benzamide [compound of formula Ib]

To a stirred solution of 2.4 g 5-chloro-2-methoxy-benzoic acid and 1.43 g tiiethylamine in 50 ml tetrahydrofuran are added at −10° dropwise 1.53 g chloroformic acid ethyl ester. The reaction mixture is stirred at −10° for 1 hour and then treated dropwise with a solution of 3.45 g 4-(4-(1,1-dimethylethyl-2-thiazolyl))-1-piperazin-ethanamine in 25 ml tetrahydrofuran. The reaction mixture is stirred at room temperature for 6–8 hours and then evaporated. The residue is partitioned between CH₂Cl₂ and 4N NaOH. The organic layer is washed with saturated brine solution, dried and evaporated to give the title compound which, recrystallized from hexane/ethyl acetate has a m.p. of 97°–98°. M.p. of the maleinate is 173°.

The starting material may be obtained as follows:

(a)
4-(4-(1,1-Dimethylethyl-2-thiazolyl))-1-piperazin-acetonitril

A mixture of 19.1 g 4-(4-(1,1-dimethylethyl-2-thiazolyl))-1-piperazine, 13.8 g K₂CO₃, 80 ml dimethylformamide and 25 ml water is treated with 7.55 g chloroacetonitrile and the resulting mixture stirred for 12 hours at room temperature. The reaction mixture is evaporated under vacuum to dryness and the residue partitioned between water and CH₂Cl₂. The organic layer is washed with water, dried and evaporated to give the heading compound, m.p. 99°–100° (from ethanol).

(b)
4-(4-(1,1-Dimethylethyl-2-thiazolyl))-1-piperazin-ethanamine

To a stirred suspension of 3.7 g lithium aluminum hydride in 250 ml abs. diethyl ether is added dropwise at 0° a solution of 17 g 4-(4-(1,1-dimethylethyl-2-thiazolyl))-1-piperazin-acetonitrile in 250 abs. diethyl ether, with the mixture maintained at −5 to +5° during the addition period. After the addition is completed, the reaction mixture is stirred for 12 hours at room temperature. The mixture is cooled to −10° and treated in portions with 400 ml 30% NaOH. The ether layer is separated, washed, dried and evaporated to give the heading compound as an oil.

EXAMPLE 9

In a manner analogous to that described in Example 8, the following compounds of formula Ib are obtained wherein W is —(CH₂)ₙ—:

| Ex. | R₁ | R₂ | R₈ | R₉ | n | m.p. |
|---|---|---|---|---|---|---|
| a | C(CH₃)₃ | H | H |  | 2 | 192–194°(2) |
| b | C(CH₃)₃ | H | CH₃ |  | 2 | 145° |
| c | C(CH₃)₃ | H | H | 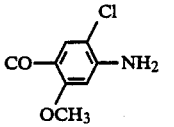 | 2 | 186–188° |
| d | C(CH₃)₃ | H | H | 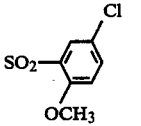 | 2 | 179–180°(2) |
| e | C(CH₃)₃ | H | H | 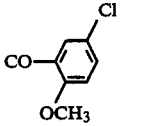 | 3 | 118–122°(2) |
| f | C(CH₃)₃ | H | H | 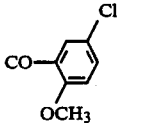 | 4 | 113–114° |
| g | C(CH₃)₃ | H | H | 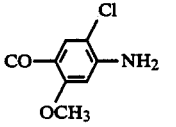 | 3 | 100–103° |
| h | C(CH₃)₃ | H | H | 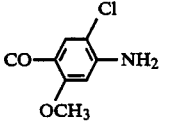 | 4 | 120° |

-continued

| Ex. | R₁ | R₂ | R₈ | R₉ | n | m.p. |
|---|---|---|---|---|---|---|
| i | C(CH₃)₃ | H | H | 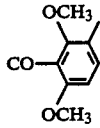 | 2 | 163–165°(2) |
| j | C(CH₃)₃ | H | H | 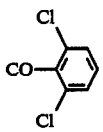 | 2 | 167° |
| k | C(CH₃)₃ | H | H | 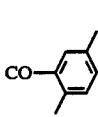 | 2 | 120–122° |
| l | C(CH₃)₃ | H | H | 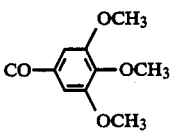 | 2 | 151–152° |
| m |  | H | H | 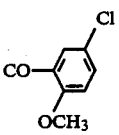 | 2 | 155–156° |
| n | CH₃ | CH₃ | H | 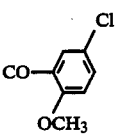 | 2 | 123–125° |
| o | C(CH₃)₃ | H | H |  | 4 | 119–120° |
| p | C(CH₃)₃ | H | H |  | 4 | 139–140°(2) |
| q | C(CH₃)₃ | H | CH₃ | 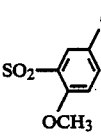 | 4 | 89–91° |
| r | C(CH₃)₃ | H | H |  | 2 | 220–223°(1) |
| s | C(CH₃)₃ | H | H | 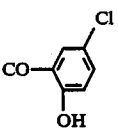 | 2 | 164–165° |
| t | C(CH₃)₃ | H | CH₃ |  | 4 | 120–122°(1) |
| u | CH₃ | H | H |  | 4 | 200–204°(5) |
| v | H | H | H |  | 4 | 114° |
| w | CH₃ | H | H | COC(CH₃)₃ | 4 | 150–151(2) |
| x | C(CH₃)₃ | H | H | COC(CH₃)₃ | 4 | 165–165(2) |

EXAMPLE 10

In a manner analogous to that described in Example 4, the following compounds of formula Ia are obtained, wherein X—Y is N—CH₂ and W is —(CH₂)ₙ—:

| Ex. | R₁ | R₂ | n | R₃ | m.p. |
|---|---|---|---|---|---|
| a | C₂H₅ | H | 4 | 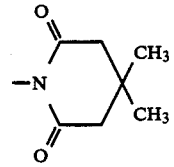 | 73–74° |
| b | CH(CH₃)₂ | H | 4 | 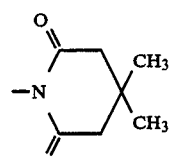 | 164–165°(2) |
| c | n-C₄H₉ | H | 4 | 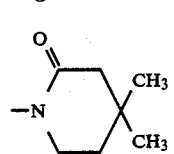 | 137–139°(2) |
| d |  | H | 4 |  | 128–131°(2) |
| e | 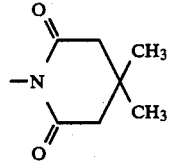 | H | 4 | | 169–170°(2) |
| f | CH₂C₆H₅ | H | 4 | | 149–150°(2) |
| g | C₂H₅ | H | 4 | 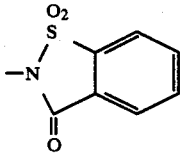 | 197–198°(1) |

-continued

| Ex. | R₁ | R₂ | n | R₃ | m.p. |
|---|---|---|---|---|---|
| h | CH(CH₃)₂ | H | 4 | 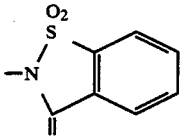 | 138°(2) |
| i |  | H | 4 | 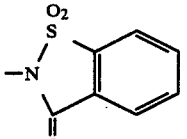 | 138–140°(3) |
| j |  | H | 4 | 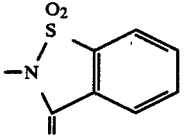 | 135–136°(2) |
| k | HC(CH₃)C₂H₅ | H | 4 | 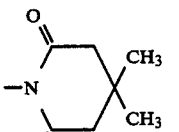 | 153–155°(2) |
| l | CH₂—CH(CH₃)₂ | H | 4 | 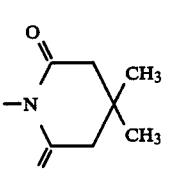 | 143–145°(2) |

EXAMPLE 11

4,4-Dimethyl-1-(4-(4-(4-(1,1-dimethylethyl)-2-thiazolyl)-1-(1,2,3,6-tetrahydropyridinyl))butyl)-2,6-piperidindione [compound of formula Ia]

In a manner analogous to that described in Example 1, the title compound is produced, m.p. of the hydrogenmaleinate is 180°–181°.

The compounds of formula I and their pharmaceutically acceptable acid addition salts exhibit pharmacological activity and are therefore indicated for use as pharmaceuticals, e.g. for therapy.

The compounds of formula I promote social interactions after acute and chronic administration of 0.3 to 10 mg/kg p.o. in male mice in aggression-evoking social encounters [A. K. Dixon, Triangle 21 (1982) 95–105; M. Krsiak, Brit. J. Pharmacol. 55 (1975) 141–150]. In this test, amitriptyline and imipramine also promote social behaviour [A. K. Dixon, Behavioural Models and the Analysis of Drug Action, Proceeds of 27th OHOLO Conference, Zichron Ya'achav, Israel, Eds. M. Y. Spiegelstein, A. Levy, Elsevier, Amsterdam (1982) 39–55].

Furthermore, the compounds of formula I show conflict reducing activity as can be shown after administration of 0.1 to 10 mg/kg p.o. of the compounds to male intruder mice [A. K. Dixon, M. Krsiak, as above].

In both the aggression as well the intruder tests, the compounds of formula I improve social interactions.

The compounds of formula I further stimulate the vigilance of test animals as can be shown in the increased spontaneous activity after administration of 0.5 to 10 mg/kg p.o. to mice according to R. Caviezel and A. Baillod [Pharm. Acta Helv. 33 (1958) 469].

Further, the compounds of formula I modify the sleep phases in the sleep/wake cycle in the rat after administration of 3 to 30 mg/kg p.o. [H. Kleinlogel, EEG in Drug Research, Ed. H. Hermann, Gustav Fischer Verlag, Stuttgart, New York, 75–88 (1982)]. In the 8h-EEG, the slow wave phase (SWS) is increased, whereas the spindle phase and the paradoxical sleep phase (PS) are reduced. In Hjorth, parameters are the mean EEG amplitude (CA) and the complexity (CCF) increased.

The decrease of paradoxical sleep phase is characteristic for antidepressants such as imipramine, desipramine, nomifensine, mianserine or dibenzepine [H. Kleinlogel, as above, page 83].

Furthermore, in the rat-8h-sleep-EEG, atypical dozing characteristic for antischizophrenics (haloperidol, clozapine) after administration of 3 to 30 mgkg p.o. is observed [A. Sayers, H. Kleinlogel, Arzneimittelforschung 24 (1974) 981–983].

Further, the compounds of formula I exhibit a strong affinity to 5HT-1A-binding sites in the pig cortex characterized by binding $^3$H-8-hydroxy-2-(di-n-propylamino)-tetraline ($^3$H-PAT) [H. Gozlan et al., Nature 305 (1983) 140; modified by A. Pazos, D. Hoyer, J. M. Palacios, Eur. J. Pharmacol. 106 (1985) 531, 539]. In this test, the compounds have an $IC_{50}$ from 1 to 600 nM, e.g. 10 to 400 nM. A group of novel anxiolytics such as buspirone and trazodone also bind at the 5HT-1A-binding sites in the pigs cortex with $IC_{50}$ values of 10 to 400 nM.

In view of their social interaction improving activity, their conflict reducing activity and their affinity for 5HT-1A-binding sites the compounds of formula I are useful as anxiolytic agents, e.g. in the treatment of conditions or disorders characterized by deficits in approach-oriented behavior and/or by anxiety.

In view of their social interaction improving activity and their vigilance increasing activity, the compounds of formula I are useful as psychogeriatric agents, e.g. in the treatment of geriatric disorders characterized by social withdrawal and reduced drive.

In view of their social interaction improving activity, their conflict reducing activity, their vigilance increasing activity, their ability to decrease the paradoxical sleep phase and their affinity for 5HT-1A-binding sites, compounds of formula I are useful as antidepressant agents, e.g. in the treatment of depressions.

In view of their social interaction improving activity, their conflict reducing activity, their vigilance increasing activity and their ability to induce atypical dozing, compounds of formula I are useful as antischizophrenic agents, e.g. in the treatment of schizophrenia.

For the above uses, the dosage required will of course vary depending on e.g. the particular compound employed, the mode of administration, the particular condition to be treated and the effect desired. In general, satisfactory results are obtained on administration of compounds of formula I at a daily dosage of:
(1) from about 0.1 to about 30 mg/kg body weight for anxiolytic and psychogeriatric activity;
(2) from about 0.3 to about 30 mg/kg body weight for antidepressant and antischizophrenic activity.

For the larger mammals, an indicated daily dosage is in the range of:

(1) from about 1 to about 500 mg and
(2) from about 25 to about 500 mg,
of compounds of formula I (for use as anxiolytic and psychogeriatric activity; antidepressant and antischizophrenic activity respectively), conveniently administered in divided doses of 2 to 4×/day in unit dosage form or in sustained release form. Suitable unit dosage forms accordingly comprise:
(1) from about 0.25 to about 250 mg and
(2) from about 5 to about 250 mg;
(according to intended utility) of compound of formula I together with one or more pharmaceutically acceptable diluents or carriers therefor.

The compounds of formula I may be administered in a similar manner to known standards for use in the cited indications.

As previously indicated a suitable daily dosage for any particular compound will depend on a number of factors including its relative potency of activity.

For example, in the above cited 5HT-1A-binding affinity test, the Example 8 compound has an IC$_{50}$ of 600 nM. In the aggression test mentioned above, the Example 8 compound at a dose of 0.3 mg/kg p.o. (acute administration) promotes social interactions. It is indicated that the compound may be administered at daily dosages of about 5 to about 200 mg p.o. to larger mammals, e.g. 5 to 50 mg, for the anxiolytic indication.

In the rat 8h-sleep-EEG mentioned above, the Example 8 compound after administration of 10 mg/kg p.o. increases slow wave phase (SWS), reduces the spindle phase and the paradoxical sleep phase (PS). The mean EEG amplitude (CA) and the complexity (CCF) were increased. It is indicated that the compound may be administered at daily dosage of about 25 to about 250 mg p.o. to larger mammals for the antidepressant indication.

In the rat 8h-sleep-EEG mentioned above the Example 8 compound shows atypical dozing after administration of 10 mg/kg p.o. It is indicated that the compound may be administered at daily dosage of about 25 to about 500 mg p.o. to larger mammals for the antischizophrenic indication.

The Example 4 and Example 8 compounds are the preferred compounds.

The compounds of formula I may be administered in free base form or in pharmaceutically acceptable acid addition salt form. Such salts may be prepared in conventional manner and exhibit the same order of activity as the free base form. The present invention also provides a pharmaceutical composition comprising a compound of formula I in free form or in salt form in association with a pharmaceutically acceptable diluent or carrier. Such compositions may be formulated in conventional manner. The compounds may be administered by any conventional route in particular enterally preferably orally e.g. in the form of tablets or capsules, or parenterally e.g. in the form of injectable solutions or suspensions.

In accordance with the foregoing, the present invention also provides a compound of formula I as hereinbefore defined for use as a pharmaceutical. i.e. for use in therapy, for example: for use as an anxiolytic or psychogeriatric; for use as an antidepressant or for use as an antischizophrenic; and especially for use in any of the specific indications hereinbefore recited in relation to such use; as well as a method of
(1) effecting anxiolytic or psychogeriatric treatment,
(2) effecting antidepressant or antischizophrenic treatment
e.g. for treating any of specific conditions hereinbefore recited in relation to such treatment, in a subject in need of such treatment, which method comprises administering to said subject an effective amount of a compound of formula I as hereinbefore defined, or a pharmaceutically acceptable acid addition salt thereof.

In a preferred group of compounds of formula I,
$R_1$ and $R_2$ independently are hydrogen, $(C_{1-6})$alkyl, $(C_{3-6})$cycloalkyl, $(C_{3-6})$cycloalkyl$(C_{1-3})$alkyl, phenyl, phenyl$(C_{1-3})$alkyl or
$R_1$ and $R_2$ signify together pentamethylene, or
$R_1$ and $R_2$ signify together —$(CH_3)_2C$—O—$C(CH_3)_2$—,
$R_1$ is additionally trifluoromethyl,
W is alkylene of 2 to 6 carbon atoms, or alkenylene or alkynylene of 4 to 6 carbon atoms, whereby the unsaturation is not adjacent to the nitrogen atoms,
X—Y is N—$CH_2$, C=CH or CH—$CH_2$,
$R_3$ is a group of formula (a), wherein A is $CH_2$, B is CO, m is 1, $R_4'$ and $R_5'$ are each hydrogen, $R_4$ and $R_5$ are each methyl or wherein A is $CH_2$, B is $CH_2$, m is 0, and $R_4$ and $R_5$ are each hydrogen; or
$R_3$ is a group of formula (b), wherein t is 4; or
$R_3$ is a group of formula (f), wherein B is CO; or
$R_3$ is a group of formula (g), wherein A is NH; or
$R_3$ is a group of formula (i), wherein E is N; or
$R_3$ is a group of formula (j), wherein A' is $CH_2$ and B is CO,
and when X—Y is N—$CH_2$, $R_3$ is also a group of formula (o), wherein $R_8$ is hydrogen or $(C_{1-3})$alkyl, $R_9$ is —$COR_{10}$ or —$SO_2R_{10}$, wherein $R_{10}$ is $(C_{1-6})$ alkyl or phenyl, wherein phenyl is optionally mono- or independently di- or trisubstituted by hydroxy, methoxy, amino or halogen, provided that when W is dimethylene and $R_9$ is —$COR_{10}$, wherein $R_{10}$ is 4-aminophenyl, at least one of $R_1$, $R_2$ and $R_8$ is other than hydrogen, and acid addition salts thereof.

I claim:
1. A compound of formula I:

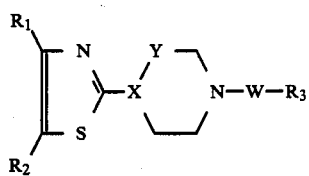

wherein
$R_1$ and $R_2$ independently are hydrogen, $(C_{1-6})$alkyl, $(C_{3-6})$cycloalkyl, $(C_{3-6})$cycloalkyl$(C_{1-3})$alkyl, phenyl, phenyl$(C_{1-3})$alkyl or
$R_1$ and $R_2$ signify together trimethylene, tetramethylene or pentamethylene, optionally substituted at the same or different carbon atoms by 1 or 2 methyl groups, or
$R_1$ and $R_2$ signify together —$(CH_3)_2C$—O—$C(CH_3)_2$—,
$R_1$ may additionally signify trifluoromethyl;
W is alkylene of 2 to 6 carbon atoms, or alkenylene or alkynylene of 4 to 6 carbon atoms, whereby the unsaturation is not adjacent to the nitrogen atoms;
X—Y is C=CH or CH—$CH_2$; and
$R_3$ is a group of formula (f)

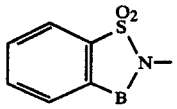

in which B is

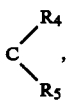

where $R_4$ is hydrogen or $(C_{1-4})$alkyl, and $R_5$ is hydrogen, $(C_{1-4})$alkyl, phenyl or phenyl$(C_{1-4})$alkyl; or is C=O;

or a pharmaceutically acceptable acid addition salt thereof.

2. A compound according to claim 1 wherein $R_1$ and $R_2$, independently, are hydrogen, $(C_{1-6})$alkyl, $(C_{3-6})$cycloalkyl, $(C_{3-6})$cycloalkyl$(C_{1-3})$alkyl, phenyl, phenyl$(C_{1-3})$alkyl, or $R_1$ and $R_2$ signify together trimethylene, tetramethylene or pentamethylene;

W is alkylene of 2 to 6 carbon atoms;

X—Y is C=CH or CH—CH$_2$; and $R_3$ is a group of formula (f) wherein B, $R_4$ and $R_5$ are as defined in claim 1;

or a pharmaceutically acceptable acid addition salt thereof.

3. A compound according to claim 1 wherein $R_1$ and $R_2$ independently are hydrogen, $(C_{1-6})$alkyl, $(C_{3-6})$cycloalkyl, $(C_{3-6})$cycloalkyl$(C_{1-3})$alkyl, phenyl, phenyl$(C_{1-3})$alkyl, or $R_1$ and $R_2$ signify together pentamethylene, or $R_1$ and $R_2$ signify together —(CH$_3$)$_2$C—O—C(CH$_3$)$_2$—, $R_1$ is additionally trifluoromethyl;

W is alkylene of 2 to 6 carbon atoms, or alkenylene or alkynylene of 4 to 6 carbon atoms, whereby the unsaturation is not adjacent to the nitrogen atoms;

X—Y is C=CH or CH—CH$_2$; and $R_3$ is a group of formula (f) wherein B is C=O;

or a pharmaceutically acceptable acid addition salt thereof.

4. A compound of claim 1 which is 2-(4-(4-(4-(1,1-dimethylethyl)-2-thiazolyl)-1-(1,2,3,6-tetrahydropyridinyl))butyl)-1,2-benzisothiazol-3-(2H)one-1,1-dioxide.

5. A pharmaceutical composition useful in treating anxiety, geriatric disorders, depressions or schizophrenia comprising a pharmaceutically acceptable carrier or diluent and a therapeutically effective amount of a compound of claim 1, or a pharmaceutically acceptable acid addition salt thereof.

* * * * *